United States Patent
Ulbrich et al.

(10) Patent No.: US 8,337,781 B2
(45) Date of Patent: Dec. 25, 2012

(54) TISSUE INFILTRATION DEVICE

(75) Inventors: Hermann Ulbrich, Bad-Schönborn-Mingolsheim (DE); Marc Konrad, Dossenheim (DE); Peter Richter, Speyer (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 276 days.

(21) Appl. No.: 12/677,915

(22) PCT Filed: Sep. 16, 2008

(86) PCT No.: PCT/EP2008/062320
§ 371 (c)(1),
(2), (4) Date: Mar. 12, 2010

(87) PCT Pub. No.: WO2009/034194
PCT Pub. Date: Mar. 19, 2009

(65) Prior Publication Data
US 2010/0216222 A1 Aug. 26, 2010

(30) Foreign Application Priority Data
Sep. 16, 2007 (DE) .......................... 10 2007 044 116

(51) Int. Cl.
*A61B 10/00* (2006.01)
(52) U.S. Cl. ....... 422/536; 422/500; 422/509; 422/68.1; 422/65; 436/180
(58) Field of Classification Search .............. 422/63–67, 422/500–503, 68.1, 509, 536; 436/180
See application file for complete search history.

(56) References Cited

U.S. PATENT DOCUMENTS
5,080,869 A 1/1992 McCormick
(Continued)

FOREIGN PATENT DOCUMENTS
DE 1007083 B 4/1957
(Continued)

OTHER PUBLICATIONS

WIPO, International Preliminary Report on Patentability issued in International Application No. PCT/EP2008/062320, Apr. 7, 2010.
(Continued)

*Primary Examiner* — Jyoti Nagpaul
(74) *Attorney, Agent, or Firm* — Hodgson Russ LLP (57) ABSTRACT

The present invention relates to a tissue infiltration device (1) for samples (34) contained in cassettes (5). The tissue infiltration device (1) comprises at least two liquid containers (7, 11a-11d, 13, 15) and a transport apparatus (6). A liquid (12, 14, 16) having a property that can be predetermined can be filled into a liquid container (7, 11a-11d, 13, 15). A plurality of cassettes (5) can be held by a transport device (4). Using the transport apparatus (6), a transport device (4) can be brought to a liquid container (7, 11a-11d, 13, 15) and/or moved away from a liquid container (7, 11a-11d, 13, 15). A sequence of operations (8) can be prescribed in which a transport device (4) runs through the liquid containers (7, 11a-11d, 13, 15) of the tissue infiltration device (1). So that an accelerated or priority processing of a transport device (4) is possible using the tissue infiltration device (1), but without using an additional liquid container (7, 11a-11d, 13, 15) provided only for this purpose, it is provided that at least two transport devices (4) can be brought into a liquid container (7, 11a-11d, 13, 15) above and/or next to one another, wherein said transport devices can have different dwell times in the liquid container (7, 11a-11d, 13, 15).

35 Claims, 5 Drawing Sheets

U.S. PATENT DOCUMENTS

| | | | |
|---|---|---|---|
| 5,895,628 A | 4/1999 | Heid et al. | |
| 6,058,788 A | 5/2000 | Thiem et al. | |
| 6,803,018 B1 | 10/2004 | Stiller | |
| 7,083,761 B2 * | 8/2006 | Zimmermann et al. | 422/536 |
| 2002/0018733 A1 | 2/2002 | Kapplein et al. | |
| 2002/0076351 A1 | 6/2002 | Wernz et al. | |
| 2002/0193814 A1 | 12/2002 | Zimmermann et al. | |
| 2004/0132068 A1 | 7/2004 | Schubert | |
| 2005/0002830 A1 | 1/2005 | Fredenburgh | |
| 2005/0059155 A1 | 3/2005 | Graupner et al. | |
| 2005/0118670 A1 * | 6/2005 | Lihl et al. | 435/40.5 |
| 2007/0243626 A1 | 10/2007 | Windeyer et al. | |
| 2008/0113440 A1 * | 5/2008 | Gurney et al. | 436/48 |
| 2008/0199955 A1 | 8/2008 | Ulbrich et al. | |

FOREIGN PATENT DOCUMENTS

| | | |
|---|---|---|
| WO | 2004059441 A2 | 7/2004 |

OTHER PUBLICATIONS

United Kingdom Examination Report under Section 18(3) issued for Application No. GB0922430.4 under the name of Leica Biosystems Nussloch GmbH dated Jul. 15, 2011; 2 pages.

* cited by examiner

TISSUE INFILTRATION DEVICE

CROSS-REFERENCE TO RELATED APPLICATIONS

The present application is the U.S. National Stage of International Application No. PCT/EP2008/062320 filed Sep. 16, 2008, which claims priority of German Application No. 10 2007 044 116.0 filed Sep. 16, 2007. The present application claims priority benefit of said International Application No. PCT/EP2008/062320 and said German Application No. 10 2007 044 116.0.

FIELD OF THE INVENTION

The present invention relates to a tissue infiltration device for samples contained in cassettes, the tissue infiltration device comprising at least two liquid containers and a transport apparatus. A liquid having a property that can be predetermined can be filled into a liquid container. A plurality of cassettes can be held by a transport device. Using the transport apparatus, a transport device can be brought to a liquid container and/or moved away from a liquid container. A sequence of operations can be prescribed in which a transport device runs through the liquid containers of the tissue infiltration device. The transport devices are inserted into the liquid container from above or, respectively, are removed upwards.

BACKGROUND OF THE INVENTION

The preparation of tissue samples for histological examinations takes place by way of several chemical treatments and by a final embedding of the sample in paraffin. During the chemical treatment, the sample is first fixed with a suitable chemical liquid, then the water contained in the sample is extracted and replaced by stabilizing agents, coloring agents and the like. Finally, the sample is embedded in paraffin or wax. What is achieved hereby is that a paraffin block can be kept stable in a receptacle of a microtome for cutting individual thin tissue sections. For different successive methods steps, so-called tissue infiltration devices or embedding machines have been developed, which automatically transport the samples into the different treatment stages.

The sample can be a biopsy, a punch or a tissue part removed during a surgery. These samples are each placed in a cassette, in which they are transported through the individual treatment steps. Merely exemplarily, the document DE 103 42 264 A1 is mentioned in which, inter alia, such a cassette is described. Eventually, these samples or thin tissue sections thereof are to be subjected to a histological examination. To this end, a pathologist observes with the aid of a microscope a sample thin section prepared with a microtome and placed on a slide, wherein the sample thin section can be dyed by means of a dyeing method and can be provided with a cover glass.

By means of the transport apparatus of the tissue infiltration device it shall in particular be possible to simultaneously transport at least two transport devices in the tissue infiltration device or to transport two transport devices that are simultaneously present in the tissue infiltration device one after the other in a time-shifted manner. By means of the transport apparatus a transport device is usually brought to a liquid container and placed into the same. By means of the transport apparatus—usually at a later point in time—the transport device is then moved out of the liquid container and away from the liquid container.

What is to be particularly understood by a sequence of operations or processing order in the sense of the present invention is that an order is predetermined or can be predetermined—for example by an operator of the tissue infiltration device —according to which a transport device with cassettes runs through the liquid containers provided in the tissue infiltration device. In this connection, a liquid container can also be considered as a processing station at which the cassettes contained in a transport device and hence the samples are brought into the liquid contained in the liquid container, as a result whereof the liquid acts on the samples. Insofar, by the expression "run through" in the sense of the present invention it is to be particularly understood:

the transport of a transport device with cassettes and hence with samples from an input station, at which a transport device is transferred to the tissue infiltration device, to the first liquid container of the sequence and into the same, the removal from the liquid container after a predeterminable reaction time, the transport of a transport device to the next liquid container and into the same etc., and, finally the transport to an output or transfer station, at which a processed transport device can be output or removed from the tissue infiltration device. A transfer station could transfer a processed transport device to an auto-embedder.

For example, from DE 196 47 662 C1, a tissue infiltration device is known in which a plurality of liquid containers are circularly arranged. To this tissue infiltration device one or, as the case may be, also more transport devices can be transferred one after the other in a time-shifted manner. These are conveyed by the transport apparatus provided therein in a predetermined sense of rotation from one liquid container to the next liquid container, wherein the transport apparatus provided therein is designed such that during one transport operation all transport devices contained in the tissue infiltration device are brought to the respective next liquid container. A complete run through of a transport device can last from one to several hours. Fully automated tissue infiltration devices can be operated automatically over night when appropriately loaded. As soon as a transport device is transferred to the tissue infiltration device a further transport device can indeed be transferred to the tissue infiltration device, but it is transported and hence processed sequentially through the individual stations or liquid containers of the tissue infiltration device in the same operational sequence as the transport device already present in the tissue infiltration device. If now the samples contained in a transport device are to be processed particularly urgently, this is not readily possible with the tissue infiltration device known from DE 196 47 662 C1 since transport devices already present in the tissue infiltration device cannot readily be removed prior to a complete run through the tissue infiltration device.

This difficulty is addressed in DE 101 63 488 A1, in which a tissue infiltration device is provided which has an additional liquid container with a smaller filling volume than the first treatment chamber. In the first treatment chamber several transport devices are processed. In the additional liquid container, a transport device can be subjected to an urgent treatment. Here, the liquid required for the respective processing step is each time filled into this liquid container and again removed after a predetermined reaction time. This indeed allows subjecting a transport device to an urgent tissue infiltration. However, it is also required, after emptying the liquid container, to first clean this liquid container before it can be filled with another liquid. This in turn is complex and requires a complex control of the filling and emptying operations of both the liquid container and the first treatment chamber. Furthermore, cleaning reagents are to be used which increase the running costs of the tissue infiltration device.

SUMMARY OF THE INVENTION

Therefore, the object of the present invention is to specify and develop a tissue infiltration device which overcomes the disadvantages mentioned above. In particular, by means of the tissue infiltration device an accelerated or priority treatment of a transport device shall be possible without however using an additional liquid container provided only for this purpose.

The inventive tissue infiltration device of the type mentioned at the beginning solves the above object. Accordingly, such a tissue infiltration device is characterized in that at least two transport devices can be brought into a liquid container above and/or next to one another, which devices can have different dwell times in the liquid container.

According to the invention it has been recognized at first that the object mentioned at the beginning can, for example, be solved in that the transport devices are stacked in a liquid container. Since, as a result thereof, the samples or cassettes held in a transport device and which are to be processed quickly can, for example, be stacked on or placed onto a transport device already present in the liquid container. To this end, the liquid container or liquid containers have to be designed and filled with liquid such that the upper transport device is immersed in the liquid of the liquid container and is thus likewise exposed to the effect of the liquid. The upper transport device can again be removed first from the liquid container by the transport apparatus and can be brought to the next liquid container so that, as a result thereof, it is possible to process samples which each require a different dwell time in the respective liquid containers in one and the same tissue infiltration device. The tissue infiltration device can be operated in a processing cycle, which is, for example, adapted to the longest dwell time of the samples in the respective liquid containers. The transport device which is to be processed quickly and is stacked on a transport device that is to be processed slower can be removed from the liquid container first and at a required point in time and can be brought into the next liquid container or can be output from the tissue infiltration device. Insofar, a transport device to be processed quickly can "overtake" another transport device which requires a longer reaction time in a liquid container so that it can run through the predetermined processing program at an earlier point in time. The transport device to be processed quickly can thus also be output from the tissue infiltration device at an earlier point in time than, for example, a transport device that has been inserted into the tissue infiltration device before and has been overtaken.

By this measure it is not necessary to provide a further liquid container, which is to be filled with liquids or chemicals as well as emptied therefrom and with which the transport device to be processed quickly is to be more or less processed in an independent program sequence. Rather, according to the invention, the liquid containers of the tissue infiltration device that are available anyway can be used, and it is usually not necessary either to fill one or more liquid containers with other liquids/chemicals—in a manner different from the normal operation of the tissue infiltration device—in order to process an "urgent" transport device faster with the tissue infiltration device. It can be useful to design one or more liquid containers of the tissue infiltration device with a greater depth than is possibly normal given conventional tissue infiltration devices so that a plurality of transport devices can be stacked, and all stacked transport devices can be immersed in the liquid. If it is merely provided to arrange the transport devices next to one another in a liquid container, it can be useful to design the cross-sectional surface of one or more liquid containers larger than is possibly normal given conventional tissue infiltration devices in order to bring at least two transport devices into one liquid container next to one another so that the transport devices arranged next to one another are immersed in the liquid. The transport devices arranged in the liquid container next to one another can be accessed independently by the transport apparatus so that, as a result thereof, an "urgent" processing of a transport device as described above is possible as well.

According to a preferred embodiment, a guide element is provided in at least one liquid container, with the aid of which two transport devices—preferably substantially congruently—can be stacked. Alternatively or additionally, a guide element could be provided in at least one liquid container, with the aid of which two transport devices can be arranged next to one another in a predeterminable manner. Particularly preferred, at least one guide element is provided in all liquid containers, with which two transport devices—preferably substantially congruently—can be stacked and/or arranged next to one another in a predeterminable manner.

The guide element could, for example, have a rod. One or, respectively, all transport devices could each have a recess, for example in a central area. The transport device can be slipped over the rod with the recess in order to stack several transport devices substantially congruently. Specifically, the rod could be arranged vertically and centrally in the liquid container, and at least one and up to a maximum number of transport devices can be slipped over the rod with their centrally provided recess and thus be (congruently) stacked in vertical direction. Alternatively or additionally, at least one further guide element could be provided which is provided laterally at the edge of a liquid container and which, for example, has a slot or rail shape. When the transport devices have a shape at the edge that is substantially complementarily designed with regard thereto, a congruent stacking of the transport devices can likewise be realized through this.

Preferably, the rod has a round, angular or circular cross-section. The recess in the transport device has a cross-section which is substantially complementary to the rod. If the rod or, respectively, the recess each has a circular cross-section, the transport device can be rotated relative to the rod about the longitudinal axis of the rod as a rotation axis. If the rod or, respectively, the recess has a round or angular non-rotation-symmetric cross-section, the transport device cannot be rotated relative to the rod, unless the rod has several segments which can be rotated relative to one another individually about the longitudinal axis of the rod as a rotation axis.

According to a particularly preferred embodiment the transport device has at least two sector portions, each of which can hold at least one cassette. This could, for example, be realized in that the transport device has individual inner walls by which the individual sector portions are defined.

The outer shape of the transport device could in particular be designed with a round, circular or angular shape. If the outer shape of the transport device is designed with an angular shape, this could be a triangular, quadrangular, hexagonal or, most general, a polygonal shape. The cross-sectional shape of a liquid container could be formed substantially comparably to the outer shape of the transport devices and thus likewise have a round, circular or angular cross-sectional shape. A circular transport device could be designed as a carousel.

According to a most particularly preferred embodiment a sector piece can be reversibly removed from the transport device in order to remove the cassette or cassettes contained in the sector piece from the transport device. As a result thereof, at least two sector pieces can be jointly transported with one transport device. However, it is likewise possible to remove a sector piece from the transport device and to replace it by another sector piece, or to let the transport device run through the tissue infiltration device without the removed sector piece—more or less with an incomplete occupation. Accordingly, the individual sector pieces which can be transported with a transport device and can each hold at least one cassette with samples can be selectively removed from the transport device or supplied to the transport device. As a result thereof, in a particularly advantageous manner a further flexibility for the prioritization of the individual samples or, respectively, cassettes is provided, which run through the tissue infiltration device with another, for example, shortened processing cycle.

So that the individual sector pieces of a transport device can be removed automatically or can be transferred to a transport device automatically, it is provided according to a particularly preferred embodiment that a sector piece can be transported by the transport apparatus. This could, for example, be realized in that the transport apparatus has a robot arm which, on the one hand, can grip the entire transport device and which, on the other hand, can grip an individual sector piece and move it in the tissue infiltration device. Alternatively, the transport apparatus could have two differently formed robot arms or one robot arm with two different gripper tools, wherein the one robot arm or the one gripper tool can only grip the transport device and the other robot arm or the other gripper tool can only grip an individual sector piece and move it in the tissue infiltration device.

According to a specific embodiment, the transport device could have a substantially tubular or sleeve-shaped center piece, on which at least one sector piece can be reversibly mounted. According to this embodiment, too, a sector piece could hold at least one cassette. In other words, the tubular or sleeve-shaped center piece serves as a support structure for the at least one sector piece that can be reversibly mounted thereon. Now, the transport device with the tubular or sleeve-shaped center piece could have a recess which is designed such that it can be slipped over a guide element designed in the form of a rod. As a result thereof, a transport device with at least one sector piece or also without sector pieces could each be slipped over the rod and thus be positioned in a liquid container or, respectively, be stacked. As a result, a transport device can thus hold several sector pieces which are circumferentially arranged next to one another with respect to the base area of the transport device (comparable to individual pieces of a cake on a cake plate). As an alternative to a substantially tubular or sleeve-shaped design of the center piece of the transport device, the center piece could have a different shape, for example, with a substantially round or angular cross-section or with a round or angular base area. The center piece has a recess with which the center piece of the transport device can be slipped over a guide element designed in the form of a rod in order to stack several transport devices.

Given such a design of the transport device and of the sector pieces, it can be useful that at least two transport devices can be stacked in a liquid container such that stacked sector pieces are substantially aligned with one another in vertical direction. As a result thereof, one or more sector pieces can be removed in an advantageous manner from the uppermost transport device arranged in a liquid container and can be allocated to a transport device arranged in another liquid container which has a free space for a sector piece, so that the cassettes or, respectively, samples which are allocated to this sector piece can run through the tissue infiltration device in an accelerated manner. Further, as a result of the vertically aligned arrangement of the sector pieces which are allocated to different transport devices, not only a sector piece of the uppermost transport device arranged in a liquid container can be removed. Rather, it is advantageously possible to also remove a sector piece of a transport device arranged below the uppermost transport device from the liquid container, when the respective space of the sector piece of the (uppermost) transport device arranged above is free and thus can be accessed by the transport apparatus. In this respect, a flexible and modular access to the individual sector pieces of the stacked transport devices is possible so that these can be individually removed or allocated.

A further flexibility for the selective access to individual sector pieces can be achieved when the guide element is designed such that individual transport devices in a liquid container can be rotated about a substantially vertical axis, for example, by means of individual rod sections that are rotatable independently of one another and are arranged coaxially relative to one another. To this end, for example, individual rod sections could have at least one area which is designed in the sense of a hollow shaft and into which or over which a further rod section can be inserted or, respectively, slipped. The individual rod sections could be sealed relative to one another with seals so that the liquid contained in a liquid container cannot escape from the liquid container between the individual rod sections. The individual rod sections could, for example, project downwardly out of the liquid container, where the individual rod sections can be selectively mechanically driven, for example, by means of an electric motor—in particular a stepper motor—with a possibly provided gear transmission or belt transmission. Insofar, for example, the transport device which is located in a liquid container in the uppermost position and has a free space for a sector piece can be rotated about a substantially vertical axis into a position such that a sector piece from the transport device arranged therebelow can be accessed by the transport apparatus from above and can be removed from the liquid container, without removing the transport device located above it or a further sector piece allocated to this transport device from this liquid container. As a result thereof, the flexibility of the access to individual samples or, respectively, cassettes which are contained in the sector pieces, is further increased in a most particularly advantageous manner.

According to a preferred embodiment, a transport device and/or a cassette and/or a sector piece each has an identification element. By means of this identification element, each of the transport devices, the cassettes or the sector pieces can be identified. The identification element could be a barcode or a machine-readable imprint or a transponder or an RFID tag (radio frequency identification tag). It could be provided that on the basis of the identification element the location or, respectively, the position of a cassette or a transport device or a sector piece within the tissue infiltration device can be determined. The remaining processing time of a cassette or a transport device or a sector piece could also be determined on the basis of the identification element. This measure can be useful if, earlier than expected, a sample or, respectively, cassette has to be accessed, wherein in this case the sample can be manually processed.

According to a most particularly preferred embodiment, the tissue infiltration device has a control device with which the transport apparatus and/or components of the tissue infiltration device can be controlled. By means of the control device, in particular the transport apparatus could be controlled such that a transport device and/or a cassette and/or a sector piece can be brought into a liquid container and remains therein for a predeterminable dwell time. Thus, by means of the control device, the transport apparatus could be controlled such that the transport devices or sector pieces to be processed by the tissue infiltration device are each transported in a predeterminable sequence of operations or order through the liquid container and, possibly, to or from a storage unit of the tissue infiltration device. The control device could be designed such that for each transport device or, respectively, for each sector piece an individual sequence of operations can be realized. Further components of the tissue infiltration device can be controlled with the control device, for example, the rotation of the individual above-mentioned rod sections could be commanded by the control device. The control device could in particular control an agitator for agitating the liquid in the liquid container or a filling and/or emptying unit of a liquid container. These could be liquid pumps and/or valves.

Most particularly preferably it is provided that priority criteria can be input and/or determined, on the basis of which the order of the transport devices/sector pieces can be determined or on the basis of which a preferred or accelerated treatment of individual transport devices/sector pieces is possible. The priority criteria could, for example, be input by an operator. Further, it is conceivable that the priority criteria are transferred via a network or from a database system to the tissue infiltration device. This could be particularly useful when the tissue infiltration device is embedded in a laboratory control system.

The order of the transport devices could now be determined and possibly changed dependent on the identification of the cassettes and/or the transport device and/or the sector piece. In addition to the information relating to the identification of the cassette or the transport device, information on the type of processing of the samples in the tissue infiltration device could be provided, which is either stored in the identification element in a suitable manner (e.g. coded) or which is, for example, transmitted via a network to the tissue infiltration device, if the identification of the respective cassette or the respective transport device or the respective sector piece is performed. To this end, at least one reading device would have to be provided in the tissue infiltration device, with which the identification elements of the cassettes or the transport device or the sector piece can be read each time. This information could be supplied to the control unit of the tissue infiltration device. The control unit could be designed such that depending on the determined information on the cassettes or the respective transport device/sector pieces the sequence of operations or a processing order of the individual transport devices/sector pieces and thus of the cassettes can be determined or predetermined, and thus they can in particular be variably guided or, with respect to a predeterminable processing target, can be guided through the liquid containers of the tissue infiltration unit in an optimized manner. Such a processing target could be a processing time of individual cassettes in the tissue infiltration device that is as short as possible. A further processing target could be a specific sequence of operations for a certain type of samples.

Preferably, a predeterminable prioritization of the individual samples and/or individual cassettes can be taken into account for the transport devices and/or for the sector pieces. This prioritization can either be manually input by an operator and, for example, be supplied to the control device of the tissue infiltration device. Alternatively, the prioritization could be provided or coded in the identification element of a cassette, a transport device or a sector piece so that the prioritization together with the remaining information of the identification element can be read out with a reading device and can be supplied to the control device of the tissue infiltration device. It is also conceivable that a prioritization for individual samples is transferred via a network and/or from a database system to the tissue infiltration device or its control device when the tissue infiltration device is, for example, embedded in a laboratory control system. In accordance with the prioritization the control device can control the transport device so that a cassette, a transport device or a sector piece is transported according to its priority in the tissue infiltration device.

It can be desirable to process a sample that has to be processed very quickly, for example a sample of a biopsy which is taken from a patient prior to a surgery, with high priority. In particular, very small biopsies can be processed in the individual liquid containers of the tissue infiltration device with very short dwell times (e.g. about 15 minutes each). In contrast thereto, largely dimensioned tissue, e.g. a surgical tissue is non-critical with respect to time. This tissue is likewise processed in the individual liquid containers of the tissue infiltration device. However, this processing can last up to five hours. Therefore, according to a preferred embodiment, predeterminable samples—namely in particular samples of small dimensions—have a comparably short dwell time in one or in all liquid containers. This can be achieved by way of the inventive stacking of the individual transport devices above one another and/or the arrangement of the individual transport devices next to one another in a liquid container or by the selective access to individual sector pieces.

So that a process flow as smooth or simple as possible can be guaranteed, it could be provided that above a transport device and/or above a sector piece which each hold cassettes with short dwell times no further transport device and/or no further sector piece is stacked in a liquid container. It could also be provided that in a liquid container at least one position for a transport device and/or for a sector piece for at least one cassette with a short dwell time is kept free. This could be taken into account by the control device of the tissue infiltration device accordingly and could be controlled by transport operations of the transport devices or, respectively, the sector pieces with the transport apparatus.

In a most particularly preferred embodiment, at least three liquid containers are provided, and in each of which at least one transport device can be inserted. Respective liquids are filled into these liquid containers. At least one transport device can be brought into such a liquid container, as a result whereof the cassettes held by the transport device are immersed into the liquid so that the liquid acts on the cassettes and the samples. The three liquid containers could advantageously be filled with liquids, each of which is suitable for fixing, for dehydrogenation or, respectively for waxing/paraffining of the samples. In this respect, these three liquid containers represent three processing stations of the tissue infiltration device, which are successively run through and which, with respect to the chemical processes proceeding therein, represent a suitable division of the processing steps of the tissue infiltration device that are in principle to be performed. This division is, inter alia, useful since the processing time for the fixing, the dehydrogenation and the waxing/paraffining of the samples each takes up about one third of the total processing time. The cycle changing time, with which a transport device is brought from one liquid container to another liquid container, would then correspond to one third of the total processing time accordingly. In this respect, it is also possible to bring a transport device to be processed quickly into the tissue infiltration device and to perform the change of the order of the transport devices in particular during a cycle change.

Basically, it is provided that the individual liquid containers or the components of the tissue infiltration device are modularly structured so that individual liquid containers can be modularly combined in an easy and cost-efficient manner to one tissue infiltration device—possibly for specific application cases. Here, the transport apparatus is preferably designed such that it can likewise be modularly extended or configured. The possibly provided control device, too, can be adapted to a modular device combination or can be extended.

As already indicated, at least one—preferably however five—liquid containers can serve for fixing the samples contained in the cassettes and, for this purpose, can be filled with a liquid suitable for fixing. One liquid container could serve for dehydrogenating the samples contained in the cassettes and, for this purpose, can be filled with at least one liquid suitable for dehydrogenation. A further liquid container could serve for waxing/paraffining the samples contained in the cassettes and, for this purpose, can be filled at least with a liquid suitable for waxing/paraffining.

It is also conceivable that at least one liquid container can be automatically filled with another liquid. This could in particular take place after a predeterminable or settable time. Thus, in particular the liquid container for the dehydrogenation could be filled each with an alcoholized liquid having a different alcohol concentration. Additionally or alternatively, the filling of the liquid container with another liquid could be possibly initiated by operator input—so to speak manually.

The liquid level of at least one liquid container and/or the filling volume of at least one liquid container could be predeterminable or settable, for example by a floor of the liquid container that is adjustable in height. As a result thereof, the effective liquid level of the liquid can finally be adapted to the respective processing step or the respective filling with transport devices, as a result whereof liquid or, respectively, chemicals can be saved.

In a most particularly preferred embodiment the transport devices run, according to a predeterminable sequence of operations, at first through the liquid container for fixing, then the liquid container for dehydrogenation and then the liquid container for waxing/paraffining. Accordingly, the liquid containers provided therefore are arranged accordingly, or are loaded with transport devices by the transport apparatus according to this sequence of operations.

Most general, the transport apparatus could have means for moving a transport device and/or several transport devices. The same could apply to a sector piece or several sector pieces. A transport apparatus could thus have elements for gripping a transport device or a sector piece. It is also conceivable that a transport device/a sector piece can be hooked in a correspondingly designed element of the transport apparatus. Further, means could be provided with which such a grip or hook element can be moved forward and/or in height. To this end, a rail system in connection with telescopic elements could be used. Most particularly preferred, however, the transport apparatus has at least one robot arm with which at least one transport device and/or one sector piece can be transported in the tissue infiltration device—and in particular can be transported or moved into and/or out of the tissue infiltration device. Such a robot arm could have a gripping or hooking element, which can be moved via an arm construction with a housing part of the tissue infiltration device in vertical and/or horizontal direction. Insofar, a transport device or a sector piece can be lifted, moved in horizontal direction and put down or brought into a liquid container. The robot arm or the transport apparatus could be designed such that a transport device or a sector piece can be transported out of the tissue infiltration device. With such a transport apparatus, a transport device/a sector piece can be supplied or transferred to a further processing device. It is also conceivable that by means of the transport apparatus the transport devices/sector pieces running through the tissue infiltration device can be placed in an output area of the tissue infiltration device. Likewise, by means of the transport apparatus transport devices/sector pieces could also be taken up from outside of the tissue infiltration device and transferred into it.

At least one storage unit could be provided which is designed such that at least one transport device and/or at least one sector piece, preferably up to five transport devices or sector pieces, can be stored therein. In the simplest case, such a storage unit could be formed by an area in which one or more transport devices (and in the following also analogously sector pieces) can be deposited or intermediately stored. The storage unit could also be designed in the form of a carousel which has several accommodating positions, for example 2 to 6 accommodating positions. In such an accommodating position a transport device/a sector piece can be accommodated in order to be intermediately stored in the storage unit. If the transport apparatus only realizes a substantially linear transport direction, the storage unit designed in the form of a carousel could be provided at a location along this transport path. If necessary, a transport device/a sector piece is transferred into the storage unit at a transfer position. By rotation of the carousel a further accommodating position of the storage unit can be brought to the location of the transfer position so that a further transport device/a further sector piece can be transferred to the storage unit. If a transport device located in the storage unit is now to be brought from the storage unit to a liquid container, the carousel is to be rotated such that the accommodating position of the transport device/the sector piece is placed at the transfer position so that the transport apparatus can take the transport device/the sector piece from the storage unit.

Specifically, the storage unit could be arranged at a liquid container. The storage unit could be effectively connected to the liquid container, which is, for example, given by the transport apparatus. In this case, it could, for example, be provided that a transport device is only brought into the storage unit when it has already been processed in the liquid container. Preferably, the storage unit is arranged at the liquid container for fixing.

Most generally it is conceivable that the order of two transport devices or the priority access to a transport device/to a sector piece can be predetermined or varied—controlled by a laboratory control system—so to speak remote-controlled. By means of such a laboratory control system, still other preparation devices could be controlled as well so that ideally an almost completely automatic sample preparation is possible. Such integration of the tissue infiltration device or of its control device could be realized by a coupling to a control computer for the laboratory control system via a network or to a database system.

Preferably, the content of at least one liquid container can be charged with energy, in particular for a predeterminable amount of time. The energy concerned is in particular heat energy or electromagnetic waves, for example, microwaves and/or ultrasound waves. The content of the liquid container to be charged with energy could comprise the liquid, a transport device contained therein and/or a sector piece contained therein and/or cassettes contained therein. It is particularly useful to charge the one liquid container with energy that is provided for waxing/paraffining since this accelerates the waxing/paraffining operation.

After the samples in the cassettes have been processed in the tissue infiltration device, usually the complete sample or all samples contained in the cassette are poured over with wax and joined to the cassette. This takes place in a so-called auto-embedder or embedder. After embedding or auto-embedding, the sample is ready for being processed or cut with a microtome. Thus, according to a preferred embodiment, the cassettes processed with the tissue infiltration device can be transferred to an auto-embedder.

BRIEF DESCRIPTION OF THE DRAWING VIEWS

There are now different possibilities for designing and developing the teaching of the present invention in an advantageous manner. With respect thereto, reference is to be made to the written description with reference to the drawing. In connection with the explanation of the preferred embodiments of the invention with reference to the drawing, also generally preferred embodiments and developments of the teaching are explained. In the drawing, all illustrations are schematic illustrations.

DETAILED DESCRIPTION OF THE INVENTION

In the Figures, like or similar components parts or assemblies are identified with identical reference signs.

Figure 1:
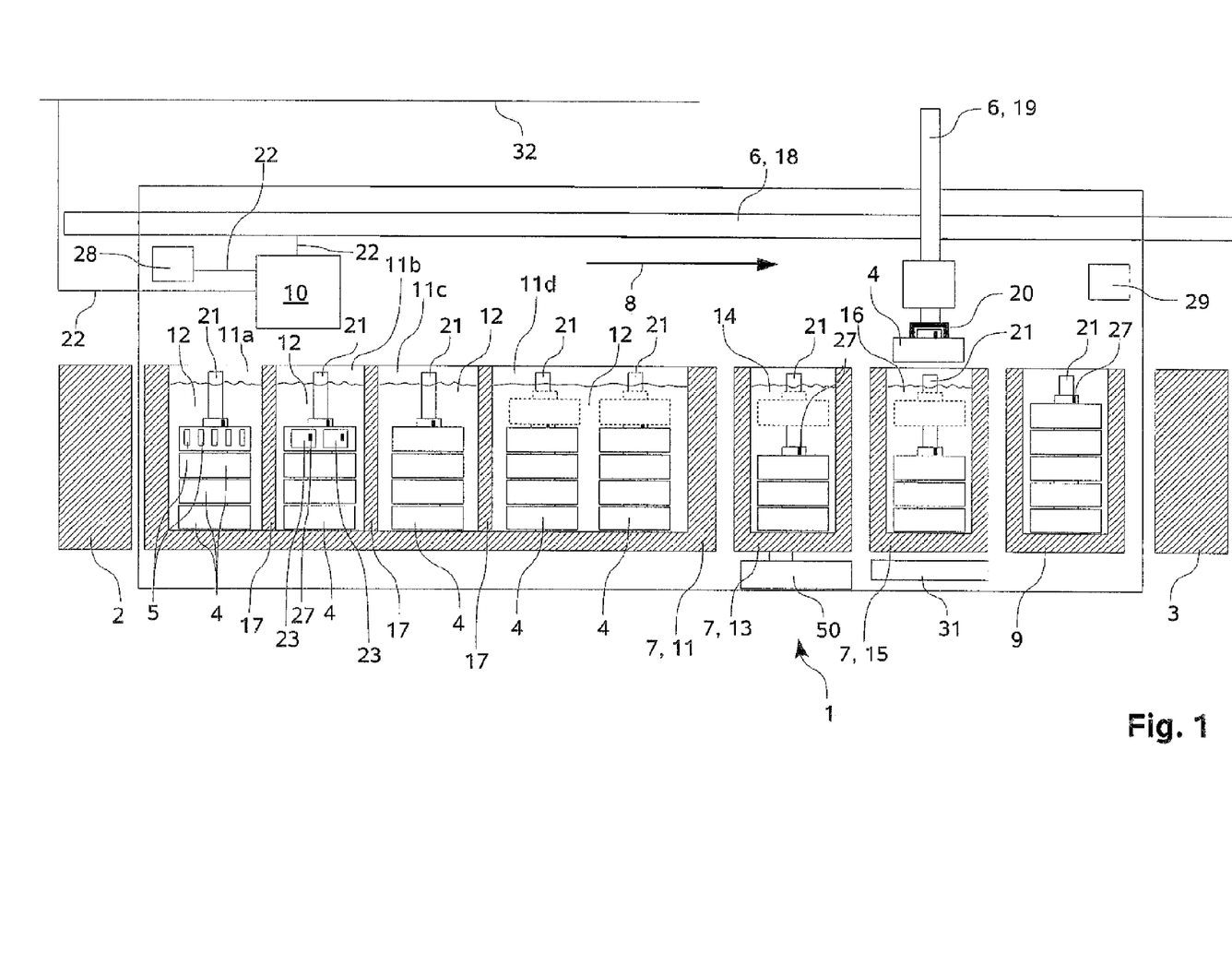
FIG. 1 shows a first embodiment of an inventive tissue infiltration device.

FIG. 1 shows an embodiment of an inventive tissue infiltration device 1. The tissue infiltration device 1 has an input station 2 and an output station 3. An operator can transfer a transport device 4 to the input station 2 of the tissue infiltration device 1. In a comparable manner, an operator can take a transport device 4 that has run through the tissue infiltration device 1 from the output station 3. Only schematically it is illustrated in one transport device 4 that a transport device 4 can hold a plurality of cassettes 5, and in the embodiment according to FIG. 1, up to 60 cassettes 5 per transport device 4. The transport devices 4 shown in FIG. 1 have a circular base area, however, alternatively, they could also have a square base area. Basically, with the tissue infiltration device 1 from FIG. 1, also transport devices 4 with a circular and with a square base area can be processed.

The tissue infiltration device 1 according to FIG. 1, further comprises a transport apparatus 6 with which a transport device 4 can be transported within the tissue infiltration device 1, and in fact from the input station 2 to the output station 3. Further, it is only schematically illustrated that the tissue infiltration device 1 has liquid containers 7, into each of which at least one transport device 4 can be brought. The transport devices 4 run through the tissue infiltration device 1 substantially from the left side to the right side in the direction of the sequence of operation 8. The tissue infiltration device 1 has a storage unit 9, in which transport devices 4 can be intermediately stored in the tissue infiltration device 1 under predeterminable conditions. Accordingly, a transport device 4 can be brought from the input station 2 or from a liquid container 7 to the storage unit 9 by the transport apparatus 6.

Further, the tissue infiltration device 1 comprises a control device 10 by means of which the transport apparatus 6 can be controlled. The control device 10 is connected via control lines 22 to the transport apparatus 6, the input station 2, the storage unit 9 and the liquid containers 7 for information exchange and for the control of these components, not all control lines 22 being shown in FIG. 1.

Specifically, three different types of liquid containers 7 are provided. The liquid container 11 serves for fixing the samples and, for this purpose, is filled with a liquid 12 suitable for fixing. The liquid container 11 has four partial containers 11a, 11b, 11c and 11d which are separated from one another by partitions 17. The four partial containers 11a, 11b, 11c and 11d can be filled with liquid 12 independently from one another. The liquid container 13 serves for dehydrogenating and can be filled with a liquid 14 suitable for this. The liquid container 15 serves for paraffining the samples and can be filled with a liquid 16 suitable for this. The transport apparatus 6 is designed in the form of a rail system and has a rail 18 for this purpose. On the rail 18, a transport arm 19 is movably guided. The transport arm 19 has a coupling element 20 with which a transport device 4 can be coupled to the transport arm 19.

According to the invention at least two transport devices 4 can be brought into one or into all liquid containers 7 above one another. The transport devices 4 brought into a liquid container 7 can have different dwell times in the respective liquid container 7. According to the invention it is likewise provided that at least two transport devices 4 can be brought into a liquid container 7 next to one another, and in fact in the partial container 11d of the liquid container 7. The transport devices 4 brought into the partial container 11d can also have different dwell times in the liquid container 7.

So that the transport devices 4 can be stacked substantially congruently, one guide element each in the form of a rod 21 is provided in every liquid container 7. So that the transport device 4 can be slipped over the rod 21, each transport device 4 has a recess which is provided in the central area of the transport device 4. The rods 21 shown in FIG. 1 as well as the corresponding recesses of the transport device 4 have a circular cross-section.

In FIG. 1, it is only schematically illustrated that a transport device 4 can immediately hold cassettes 5. Alternatively, it is also possible that the transport device 4 can hold several sector pieces 23, wherein the sector pieces 23 can be taken away from the transport device 4. A sector piece 23 can hold a plurality of cassettes 5. The transport apparatus 6 and in particular the coupling element 20 are designed such that they can transport both a transport device 4 and a sector piece 23.

Figure 2:
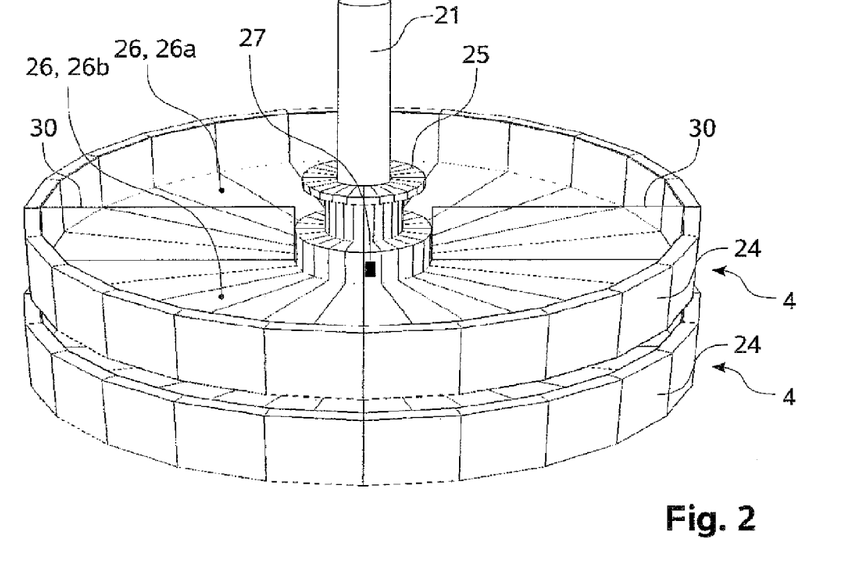
FIG. 2 is a perspective view of a first embodiment of a transport device.

FIG. 2 shows in a perspective view an embodiment of a transport device 4, into which individual cassettes 5 or sector pieces 23 can be brought so that with a transport device 4 from FIG. 2 individual cassettes 5 and/or sector pieces 23, each of which can hold at least one cassette 5, can be jointly transported. The transport device 4 from FIG. 2 has a substantially circular base area as well as an outer edge 24. In the central area of the transport device 4 a circular flange piece 25 is provided which can be gripped by the coupling element 20 of the transport apparatus 6. The inner area 26 of the transport device 4 serves for accommodating individual cassettes 5 and one or more sector pieces 23. In FIG. 2, a rod 21 is illustrated, over which two transport devices 4 are slipped. Likewise schematically illustrated is a partition 30 provided in the inner area 26 of the transport device 4, with which the inner area can be divided into two sector portions 26a, 26b. As a result thereof, for example into the sector portion 26a only cassettes 5 can be brought and into the sector portion 26b one or more sector pieces 23 can be brought.

Figure 3:
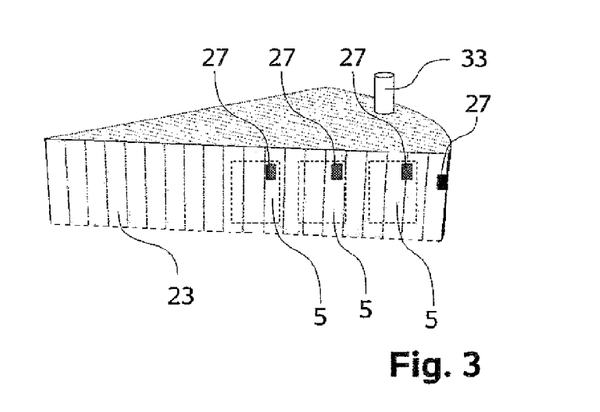
FIG. 3 is a perspective view of an embodiment of a sector piece which can be held by a transport device.

FIG. 3 shows in a perspective view a sector piece 23, the shape of which can substantially be compared to a piece of cake. The sector piece 23 can hold a plurality of cassettes 5, which is indicated by the broken line contours of the cassettes 5. The sector piece 23 has a coupling element 33, with which the sector piece 23 can be gripped by the coupling element 20 of the transport apparatus 6. Accordingly, the sector piece 23 can be separately transported by the transport apparatus 6.

Figure 4:
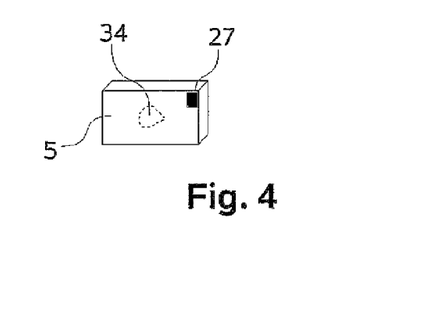
FIG. 4 is a perspective view of a cassette in which a sample can be held.

FIG. 4 shows, only schematically, an embodiment of a cassette 5 into which a tissue sample 34 is placed. The cassette 5 has grid walls with grid openings not shown in FIG. 4, through which liquids of the individual liquid containers 7 can reach into the cassette 5 and can thus act on the tissue sample 34. The cassette 5 from FIG. 4 is designed comparably to the cassette known from DE 103 42 264 A1.

Only schematically it is shown that the identification element designed in the form of a transponder 27 is provided on the transport devices 4. Also on the sector pieces 23 and on the cassettes 5, transponders 27 are provided each. In the identification element information on the identity of the transport device 4, the sector pieces 23 or, respectively, the cassettes 5 as well as the cassettes 5 and hence samples (not shown) contained therein can be stored. Further, information on the processing steps can be stored in the transponder 27, with which the samples are to be processed or were processed. Also information on the prioritization of the processing of the individual samples contained in the transport device 4 or, respectively, transport devices 4 can be stored in the transponder 27. With the reading unit 28 shown in FIG. 1, the information stored in the transponder 27 can be read out contact-free and can be transferred to the control unit 10. Dependent on the information read out from the transponder 27 of a transport device 4 or a sector piece 23, the control unit 10 can then plan the processing steps for this transport device 4 or, respectively, this sector piece 23 and perform them accordingly. Near the output station 3, there is a writing unit 29, with which information on the individual processing steps, which a transport device 4 or a sector piece 23 has run through in the tissue infiltration device 1, can be written into the respective transponder 27.

Figure 5:
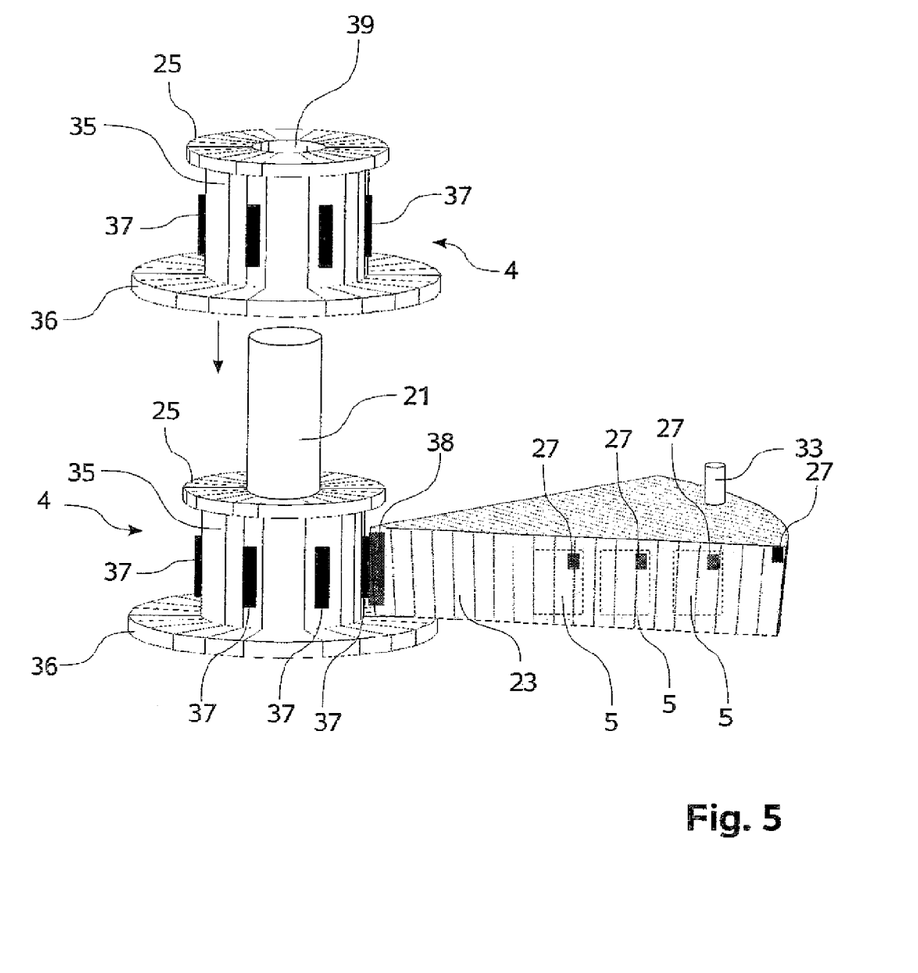
FIG. 5 is a perspective view of a second embodiment of a transport device.

FIG. 5 shows a further embodiment of a transport device 4. The transport device 4 has a center piece 35 designed in a substantially sleeve-shaped manner, which comprises in the upper area a circular flange piece 25 to be gripped by the coupling element 20 of the transport apparatus 6. In a lower area, the transport device 4 comprises a circular disk 36 on which sector pieces 23, which are mounted on the transport device 4, can be supported at least in part. The sleeve-shaped center piece 35 further comprises mounting elements 37 which cooperate with corresponding mounting elements 38 provided on the sector pieces 23. Accordingly, a sector piece 23 with its mounting element 38 can be mounted on one of the mounting elements 37 of the transport device 4. Thus, altogether 8 sector pieces 23 can be mounted on the sleeve-shaped center piece 35 of the transport device 4 from FIG. 5 and can be transported together with this transport device 4. The lower transport device 4 shown in FIG. 5 is already slipped over the rod 21. The upper transport device 4, at which, in the operating state shown in FIG. 5, no sector piece is mounted, is slipped over the rod 21 from above. At the upper transport device 4, the recess 39 can be seen which has a circular cross-section and is thus formed substantially complementarily to the circular cross-section of the rod 21.

Figure 6:
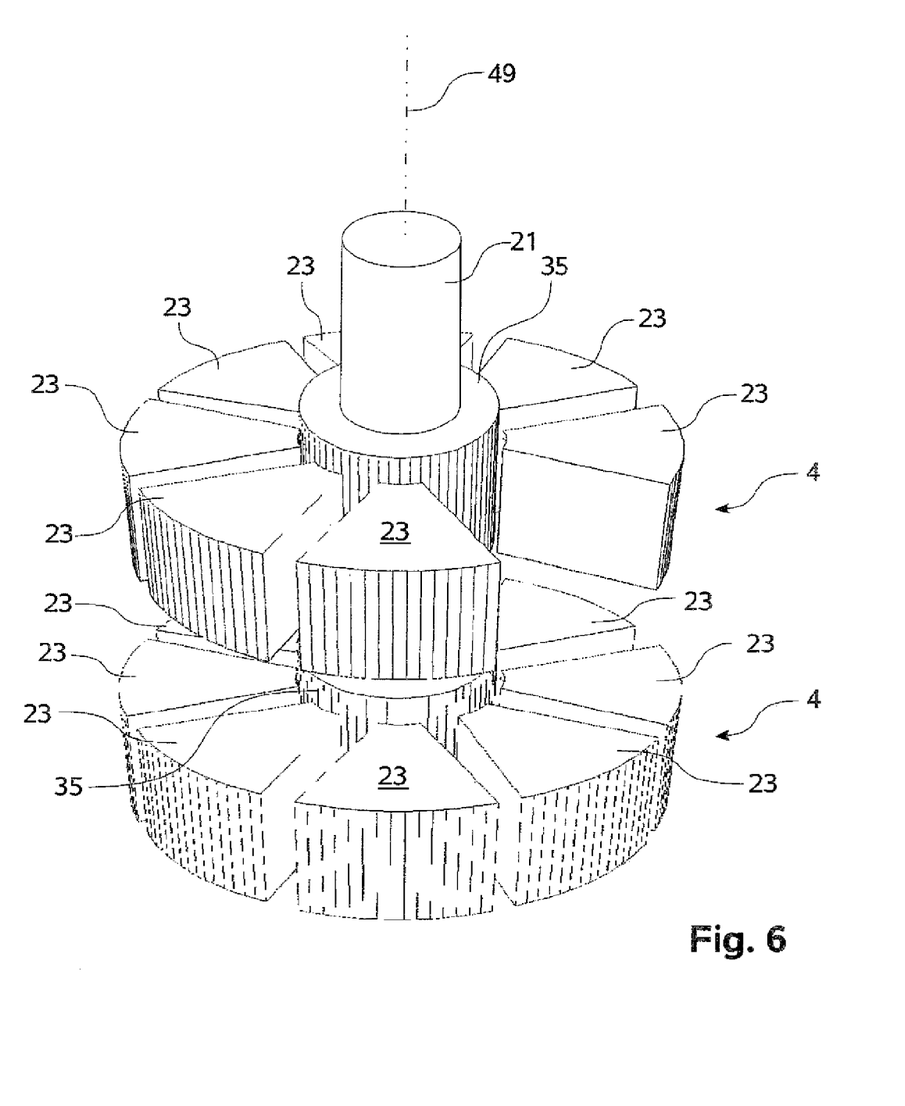
FIG. 6 is a perspective view of two stacked transport devices with individual sector pieces.

FIG. 6 shows in a schematic illustration a perspective view of two transport devices 4 slipped over a rod 21 and thus stacked above one another. Individual details of the transport devices 4, such as the circular flange piece 25, mounting elements 37, 38, the transponders 27 and the coupling elements 33 of the sector pieces 23 are not illustrated in FIG. 6 for reasons of clarity. The lower transport device 4 is loaded with altogether eight sector pieces 23. The upper transport device 4 only carries seven sector pieces 23. The sector pieces 23 of the lower transport device 4 are vertically aligned with respect to the sector pieces 23 of the upper transport device 4. Insofar by means of the transport apparatus 6 not shown in FIG. 6 or, respectively, with the transport arm 19, the sector piece 23 of the lower transport device 4 can be accessed, which is arranged below the free space of the upper transport device 4.

Figure 7:
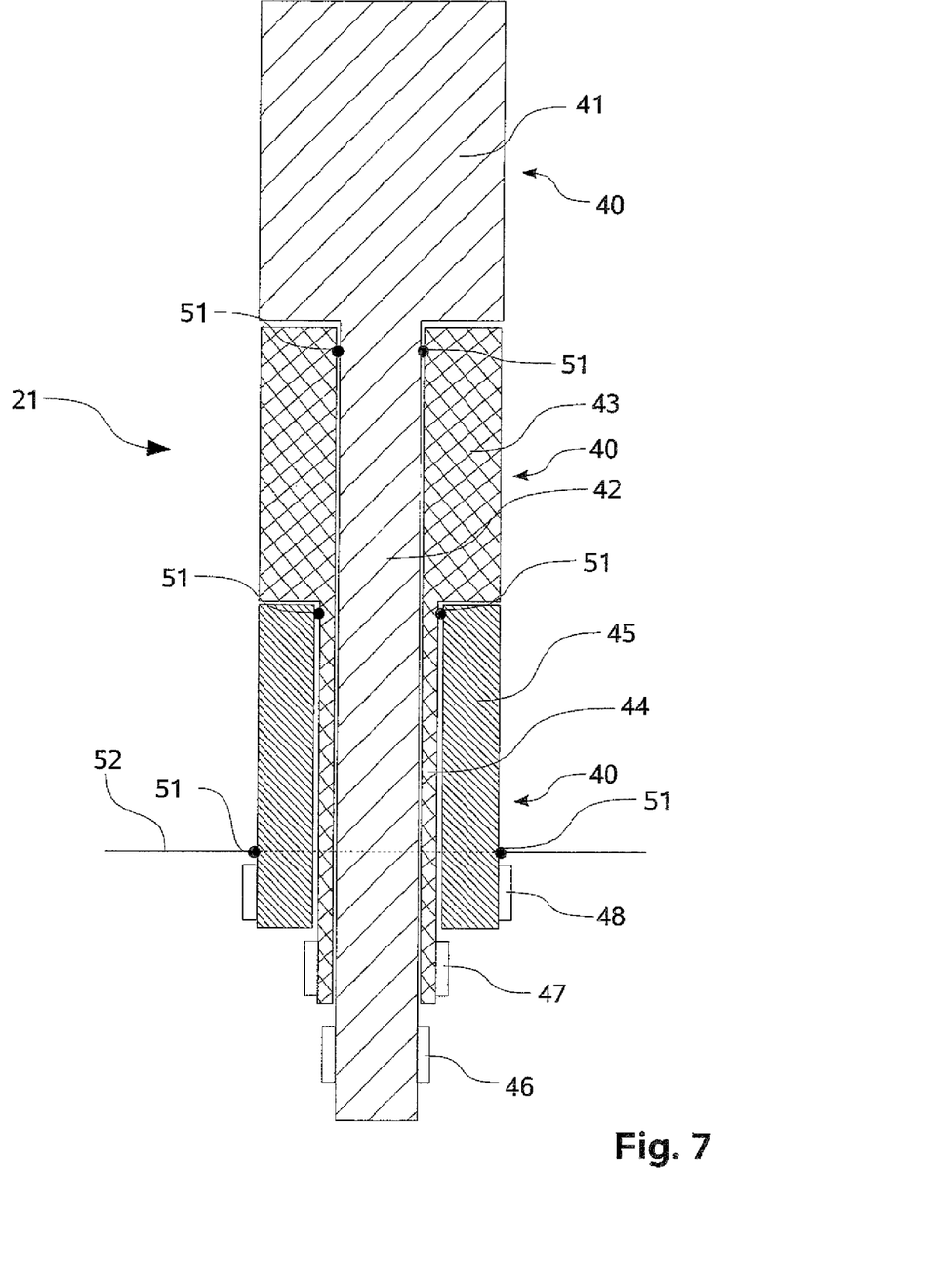
FIG. 7 is a sectional view of an embodiment of a guide element designed in the form of a rod having several rod sections.

Now, the rod 21 from FIG. 6 can be composed of several individual rod sections 40. This is schematically illustrated in FIG. 7 in cross-section. An upper rod section 41 is shown here, which has a middle and downwardly extending shaft area 42. Coaxially thereto, a middle rod section 43 is slipped over the middle shaft area 42 of the upper rod section 41 and can be rotated individually or separately from the upper rod section 41. The middle rod section 43 has a middle and downwardly extending hollow shaft area 44. Finally, a lower rod section 45 is slipped over the middle hollow shaft area 44 of the middle rod section 43, which has a substantially tubular shape. Each of the rod sections 41, 43, and 45 has, at the respective lower area which projects out of the liquid container and is arranged beyond the floor 52, a toothing 46, 47 and 48, each of which is selectively engaged with toothed wheels (not shown) and can selectively be operated by at least one electric motor that is likewise not shown. In this respect, the individual rod sections 41, 43 and 45 of the rod 21 shown in FIG. 7 can be rotated individually and separately from one another. As a result thereof, the upper or the lower transport device 4 from FIG. 6 can advantageously be brought into a position that is rotated with respect to the vertical rotation axis 49 (which corresponds to the longitudinal axis of the rod 21), so that in an advantageous manner, arbitrary sector pieces 23 of both the upper and the lower transport device 4 can be selectively accessed. If a sector piece 23 of the lower transport device 4 is to be accessed, the upper transport device 4 must have at least one free space for a sector piece 23. The rod sections 41, 43 and 45 have seals 51 in the intermediate spaces so that the liquid contained in the liquid container cannot escape from the liquid container. More than three rod sections could be provided.

Although in FIG. 1 the transport apparatus 6 is based on a rail 18 or a rail system, a robot arm (not shown) could perform the transport of the transport devices 4 and/or sector pieces 23 within the tissue infiltration device 1.

Now, the control device 10 can control the transport apparatus 6 such that in one or in all liquid containers 7 the respective uppermost position for transport devices 4 remains free, which transports cassettes 5 or, respectively, samples which require an urgent processing by means of the tissue infiltration device 1. This is indicated in FIG. 1 in that in the liquid containers 11d, 13 and 15 the respective uppermost position is illustrated with a transport device 4 shown in broken lines. As a result, a transport device 4 to be urgently processed can overtake another transport device 4 which is arranged in a lower position in one of the liquid containers 7.

Only schematically it is illustrated that the liquid 14 of the liquid container 13 serving for dehydrogenation can be replaced, a replacement device 50 being provided for this purpose. It comprises pumps (not shown) and valves (not shown) and is connected to the liquid container 13 via two line connections. A heat unit 31 designed in the form of a microwave is provided on the liquid container 15, with which the liquid 16 in the liquid container 15 and hence also the samples can be charged with heat energy. As a result thereof, the paraffining operation can be accelerated.

The tissue infiltration device 1 according to FIG. 1 is integrated via the network connection 32 in a laboratory control system not shown in the Figures, which system has a control computer and is connected to a database system, in which inter alia patient data are stored.

Finally, it is most particularly pointed out that the above explained embodiments merely serve for describing the claimed teaching but do not restrict the same to these embodiments.

List Of Reference Signs 1 tissue infiltration device
2 input station
3 output station
4 transport device
5 cassettes
6 transport apparatus
7 liquid container
8 sequence of operations
9 storage unit
10 control device
11 liquid container serving for fixing
11a-11d partial containers of (11)
12 fixing liquid
13 liquid container serving for dehydrogenation
14 dehydrogenating liquid
15 liquid container serving for paraffining
16 paraffin
17 partition
18 rail
19 transport arm
20 coupling element of (19)
21 rod
22 control lines
23 sector piece
24 edge of (4)
25 circular flange piece of (4)
26 area of (4) for accommodation of (5) and/or (23)
26a, 26b sector portions of (4)
27 transponder
28 reading unit
29 writing unit
30 partition of (4), with which (26a) and (26b) are formed
31 heat unit
32 network connection
33 coupling element of (23)
34 tissue sample
35 sleeve-shaped center piece of (4)
36 circular disk
37 mounting element on (35)
38 mounting element on (23)
39 recess on (4) for (21)
40 rod section of (21)
41 upper rod section
42 middle shaft area of (41)
43 middle rod section
44 middle hollow shaft area of (43)
45 lower rod section
46 toothing of (41)
47 toothing of (43)
48 toothing of (45)
49 rotation axis of (41, 43, 45) or longitudinal axis of (21)
50 replacement device
51 seal
52 floor of a liquid container

The invention claimed is:

1. A tissue infiltration device for samples contained in cassettes, the tissue infiltration device comprising:
at least two liquid containers (7, 11a-11d, 13, 15) for containing a respective liquid (12, 14, 16),
a plurality of transport devices (4), each transport device (4) operable to hold a plurality of cassettes (5),
a transport apparatus (6) by which the transport device (4) can be brought to a liquid container (7, 11a-11d, 13, 15) and moved away from a liquid container (7, 11a-11d, 13, 15), and
a control device (10) configured to control the transport apparatus (6) to perform a predetermined sequence of operations (8) in which a transport device (4) runs through the liquid containers (7, 11a-11d, 13, 15) of the tissue infiltration device (1)
wherein the control device is configured to bring at least two transport devices (4) above or next to one another in at least one of the liquid containers (7, 11a-11d, 13, 15), such that the at least two transport devices have different dwell times in such liquid container (7, 11a-11d, 13, 15).

2. The tissue infiltration device according to claim 1, wherein the at least one liquid container (7, 11a-11d, 13, 15) includes a guide element (21), wherein with the aid of the guide element (21) two transport devices (4) can be stacked or arranged next to one another.

3. The tissue infiltration device according to claim 2, wherein the guide element has a rod (21), the transport device (4) has a recess (39) sized to receive the rod, whereby the transport device (4) can be slipped over the rod (21) in order to stack several transport devices (4) substantially congruently.

4. The tissue infiltration device according to claim 3 wherein the rod (21) has a round, angular or circular cross-section and the recess (39) of each transport device (4) has a cross-section that is substantially complementary to the rod (21).

5. The tissue infiltration device according to claim 3, wherein each transport device (4) has at least two sector portions (26a, 26b), wherein each of the sector portions can hold at least one cassette (5), and wherein each transport device (4) has a round, a circular or an angular shape.

6. The tissue infiltration device according to claim 5, wherein each transport device (4) includes at least one sector piece (23) for holding at least one cassette (5), wherein the sector piece (23) can be reversibly removed from the transport device (4) in order to remove the cassette (5) contained in the sector piece (23) from the transport device (4).

7. The tissue infiltration device according to claim 6, wherein the at least one sector piece (23) can be transported by the transport device (4).

8. The tissue infiltration device according to claim 6, wherein each transport device (4) has a substantially tubular or sleeve-shaped center piece (35), on which at least one sector piece (23) can be reversibly mounted.

9. The tissue infiltration device according to claim 8, wherein the tubular or sleeve-shaped center piece (35) of the transport device (4) is sized to be slipped over the rod (21).

10. The tissue infiltration device according to claim 6, wherein at least two transport devices (4) can be stacked in a liquid container (7, 11a-11d, 13, 15) such that stacked sector pieces (23) of the at least two transport devices are substantially vertically aligned.

11. The tissue infiltration device according to claim 6, wherein a transport device (4) and/or a cassette (5) and/or a sector piece (23) each has an identification element (27) with which the transport device (4), the cassette (5) or the sector piece (23) can each be identified.

12. The tissue infiltration device according to claim 11, wherein the identification element has at least one element selected from a group consisting of an RFID transponder (27), a barcode, and a machine-readable imprint.

13. The tissue infiltration device according to claim 11 wherein, on the basis of the identification element (27), the location of a cassette (5) or a transport device (4) or a sector piece (23) within the tissue infiltration device (1) can be determined and/or that on the basis of the identification element (27) the remaining processing time of a cassette (5) or a transport device (4) or a sector piece (23) can be determined.

14. The tissue infiltration device according to claim 6, further comprising a control device (10) operable to control the transport apparatus (6) to bring a transport device (4) and/or a sector piece (23) into one of the liquid containers (7, 11a-11d, 13, 15) and allow such transport device (4) and/or sector piece (23) to remain therein for a predeterminable dwell time and wherein the control device (10) is operable to control further components of the tissue infiltration device (1) wherein the further components include a filling and/or emptying unit (30) of a liquid container (13).

15. The tissue infiltration device according to claim 14, characterized in that priority criteria can be input and/or determined, on the basis of which criteria the order of a transport device (4) can be determined.

16. The tissue infiltration device according to claim 15, further comprising a reading unit (28) with which an identification element (27) can be read out and can be supplied to the control device (10) of the tissue infiltration device (1).

17. The tissue infiltration device according to claim 15, wherein the control device (10) is operable to determine a processing order for the transport devices (4) and/or for the sector pieces (23).

18. The tissue infiltration device according to claim 17, wherein the control device (10) takes into account the priority criteria in determining the processing order for the transport devices (4) and/or for the sector pieces (23).

19. The tissue infiltration device according to claim 14, wherein the control device (10) is operable to provide cassettes (5) holding samples (34) having relatively small dimensions a comparably short dwell time in one of the liquid containers (7, 11a-11d, 13, 15).

20. The tissue infiltration device according to claim 19, wherein the control device (10) prevents further transport devices (4) and/or sector pieces (23) from being stacked above the transport device (4) and/or the sector piece (23) with cassettes having short dwell times in the liquid container (7, 11a-11d, 13, 15).

21. The tissue infiltration device according to claim 19, wherein the control device (10) ensures that in a liquid container (7, 11a-11d, 13, 15) at least one position for a transport device (4) and/or for a sector piece (23) for at least one cassette (5) with a short dwell time is kept free.

22. The tissue infiltration device according to claim 15, wherein according to a predeterminable sequence of operations (8), the transport devices (4) first run through a liquid container (11a-11d) for fixing, then through a liquid container (13) for dehydrogenation and then through a liquid container (15) for waxing/paraffining.

23. The tissue infiltration device according to claim 6, wherein the transport apparatus (6) has at least one robot arm, with which a transport device (4) and/or a sector piece (23) can be transported into the tissue infiltration device (1) and/or transported out of the tissue infiltration device (1).

24. The tissue infiltration device according to claim 6, further comprising a storage unit (9 designed to store at least one transport device (4) and/or at least one sector piece (23).

25. The tissue infiltration device according to claim 24, wherein the storage unit (9) is arranged on one of the liquid containers (7, 11a-11d, 13, 15).

26. The tissue infiltration device according to claim 2, wherein the guide element (21) includes a plurality of individual, separately rotatable and coaxially arranged rod sections (41, 43, 45) such that individual transport devices (4) can be rotated in the corresponding liquid container (7, 11a-11d, 13, 15) about a substantially vertical axis.

27. The tissue infiltration device according to claim 1, wherein at least one liquid container (11a-11d) serves for fixing the samples contained in the cassettes (5) and, for this purpose, can be filled with a liquid (12) suitable for fixing.

28. The tissue infiltration device according to claim 1, wherein a liquid container (13) serves for dehydrogenation of the samples contained in the cassettes (5) and, for this purpose, can be filled with at least one liquid (14) suitable for dehydrogenation.

29. The tissue infiltration device according to claim 1, wherein a liquid container (15) serves for waxing/paraffining of the samples contained in the cassettes (5) and, for this purpose, can be filled with at least one liquid (16) suitable for waxing/paraffining.

30. The tissue infiltration device according to claim 29, further comprising a heat unit (31) associated with one of the liquid containers (15) and operable such that the content of at least one liquid container (15) can be charged with energy.

31. The tissue infiltration device according to claim 30, wherein the heat unit (31) is associated with the liquid container (15) for waxing/paraffining.

32. The tissue infiltration device according to claim 1, wherein at least one liquid container (13) can be filled with another liquid automatically or by an operator input or initiated by the control device (10).

33. The tissue infiltration device according to claim 1, wherein at least one of the liquid containers (7, 11a-11d, 13, 15) includes a floor that is adjustable in height to set a liquid level and/or filling volume of such liquid container.

34. The tissue infiltration device according to claim 1, wherein the tissue infiltration device is adapted for integration into a laboratory control system by coupling to a control computer for the laboratory control system via a network (32) or to a database system.

35. The tissue infiltration device according claim 1, wherein the cassettes (5) processed with the tissue infiltration device (1) can be transferred to an auto-embedder.

* * * * *